United States Patent
Hao et al.

(10) Patent No.: US 8,699,765 B2
(45) Date of Patent: Apr. 15, 2014

(54) REDUCING JITTERING IN MEDICAL DIAGNOSTIC ULTRASOUND IMAGING

(75) Inventors: Xiaohui Hao, Blaine, WA (US); Xiangfang Li, Sunnyvale, CA (US); Lei Sui, Newcastle, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1308 days.

(21) Appl. No.: 11/983,579

(22) Filed: Nov. 9, 2007

(65) Prior Publication Data

US 2008/0175453 A1 Jul. 24, 2008

Related U.S. Application Data

(60) Provisional application No. 60/858,744, filed on Nov. 13, 2006.

(51) Int. Cl.
 - *G06K 9/00* (2006.01)
 - *G06T 7/00* (2006.01)
 - *A61B 8/00* (2006.01)

(52) U.S. Cl.
 CPC ............... *G06T 7/0012* (2013.01); *A61B 8/00* (2013.01); *G06K 9/00* (2013.01)
 USPC ............ 382/128; 382/275; 600/437; 600/443

(58) Field of Classification Search
 CPC ........... G06T 7/0012; A61B 8/00; G06K 9/40
 USPC ............................. 382/128, 275; 600/437, 443
 See application file for complete search history.

(56) References Cited

U.S. PATENT DOCUMENTS

| | | | |
|---|---|---|---|
| 5,054,045 A | 10/1991 | Whiting et al. | |
| 5,457,728 A | 10/1995 | Whiting et al. | |
| 5,822,391 A | 10/1998 | Whiting et al. | |
| 6,012,458 A * | 1/2000 | Mo et al. | 600/437 |
| 6,059,727 A * | 5/2000 | Fowlkes et al. | 600/443 |
| 6,117,081 A | 9/2000 | Jago et al. | |
| 6,126,598 A * | 10/2000 | Entrekin et al. | 600/437 |
| 6,193,660 B1 | 2/2001 | Jackson et al. | |
| 6,283,917 B1 | 9/2001 | Jago et al. | |
| 6,352,508 B1 | 3/2002 | Pang et al. | |
| 6,364,835 B1 | 4/2002 | Hossack et al. | |
| 6,423,004 B1 | 7/2002 | Dong et al. | |
| 6,527,717 B1 | 3/2003 | Jackson et al. | |
| 6,589,176 B2 * | 7/2003 | Jago et al. | 600/443 |
| 6,641,536 B2 | 11/2003 | Hossack et al. | |
| 8,105,239 B2 * | 1/2012 | Specht | 600/446 |
| 2005/0203395 A1 | 9/2005 | Sui et al. | |
| 2007/0055158 A1 | 3/2007 | Jackson et al. | |
| 2007/0129631 A1 | 6/2007 | Ma et al. | |
| 2007/0196007 A1 | 8/2007 | Chen et al. | |
| 2007/0206880 A1 | 9/2007 | Chen et al. | |
| 2007/0255137 A1 | 11/2007 | Sui et al. | |

OTHER PUBLICATIONS

Ha et al., "Determination of an Optimal Image Frame Interval for Frame-to-Frame Ultrasound Image Motion Tracking", Mar. 2005, IEEE Trans. on Ultrasonics, Ferroelectrics, and Frequency Control, vol. 52, No. 3, 386-396.*

Bohs et al., "Ensemble Tracking for 2D Vector Velocity Measurement: Experimental and Inital Clinical Results", 1998, IEEE Trans. on Ultrasonics, Ferroelectrics, and Frequency Control, vol. 45, No. 4, 912-924.*

Ledesma-Carbayo et al., "Spatio-temporal nonrigid registration for ultrasound cardiac motion estimation", Aug. 2005, IEEE Trans. on Medical Imaging, vol. 24, Iss. 9, 1113-1126.*

\* cited by examiner

*Primary Examiner* — Jason M Repko
*Assistant Examiner* — Katrina Fujita

(57) ABSTRACT

Jittering in medical diagnostic ultrasound imaging is reduced, such as in steered spatial compounding. A pattern of decorrelation is used to detect motion between component frames, register component frames, and/or reduce jitter in the motion correction. The ultrasound imaging adapts as a function of the pattern.

21 Claims, 6 Drawing Sheets

REDUCING JITTERING IN MEDICAL DIAGNOSTIC ULTRASOUND IMAGING

RELATED APPLICATIONS

This application claims the benefit of the filing date under 35 U.S.C. §119(e) of Provisional U.S. Patent Application Ser. No. 60/858,744, filed Nov. 13, 2006, which is hereby incorporated by reference.

BACKGROUND

The present embodiments relate to ultrasound imaging. In particular, jittering in medical diagnostic ultrasound imaging is reduced.

In ultrasound imaging, spatial compounding is used in extended field of view and/or steered compounding for speckle reduction. Different component frames of data associated with spatial differences (e.g., different steering angle or transducer position) are acquired and combined. However, this spatial compounding suffers from motion artifacts. Because frames are acquired at different times, and each frame takes a certain amount of time to acquire, movement of the tissue or probe can cause mis-registration between frames. When frames are compounded, the compounded image will be smeared or blurred. If the user is searching for a target region by moving the transducer, the blurring is even more pronounced.

To reduce blurring, the mis-registration errors between compounding frames caused by motion are corrected by registering the component frames to each other prior to compounding. Global and/or local displacement information between two images is estimated, such as by cross-correlation, block matching, maximum brightness, and/or feature extraction and tracking. One or both images are warped and/or aligned to make them congruent with each other. However, these solutions assume that the component frames have correlated speckle patterns or are fairly similar. The detail features (e.g., speckle pattern) for images acquired from different steering angles may be uncorrelated due to the differences between a skewed point spread function (steered beam) and a non-skewed point spread function (non-steered beam). Features, like acoustic shadows, have angle and position dependency per incident angle of ultrasonic wave, causing mis-registration. Transducer motion in an elevation direction or tilting may result in the frames having no speckle correlation and similarity at all, causing registration failure. During the scan, the clinicians may squeeze the tissue by putting some pressure on the transducer, causing mis-registration.

Variation in the imaging may cause jittering artifacts in the motion correction. Changes in the steering angle and/or region to be imaged may result in variation in registration, creating an "earthquake" effect.

BRIEF SUMMARY

By way of introduction, the preferred embodiments described below include methods, systems, computer readable media, and instructions for reducing jittering in medical diagnostic ultrasound imaging. A pattern of decorrelation is used to detect motion between component frames, register component frames, and/or reduce jitter in the motion correction. The ultrasound imaging adapts as a function of the pattern.

In a first aspect, a method is provided for reducing jittering in medical diagnostic ultrasound imaging. A pattern of decorrelation through a sequence of frames of ultrasound data is determined. Ultrasound imaging adapts as a function of the pattern.

In a second aspect, a computer readable storage medium has stored therein data representing instructions executable by a programmed processor for reducing jittering in medical diagnostic ultrasound imaging. The storage medium includes instructions for identifying a jitter in motion estimation for a sequence of frames of ultrasound data associated with different steering angles, reducing the jitter in the motion estimation, and compounding the frames of the sequence as a function of the motion estimation with reduced jitter.

In a third aspect, a computer readable storage medium has stored therein data representing instructions executable by a programmed processor for reducing jittering in medical diagnostic ultrasound imaging. The storage medium includes instructions for acquiring, with a substantially stationary transducer, first component frames of data for steered spatial compounding, the component frames of data corresponding to different steering angles, determining a first decorrelation pattern across the first component frames, acquiring second component frames of data corresponding to the different steering angles, determining a second decorrelation pattern across the second component frames, and detecting motion of the transducer for the second component frames as a function of the first and second decorrelation patterns.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF SPECIFIC EMBODIMENTS

Blurring is undesired. To reduce the blurring, motion is detected and then corrected. For steered compounding or other compound imaging, motion detection is complicated due to the different imaging angles, which decorrelate speckle patterns. The decorrelation often causes fluctuation in the correlation based motion detection.

One source of blurring is out-of-plane transducer motion. Out-of-plane motion may be detected by decorrelation between frames of data. If sufficient decorrelation occurs, then the frame of data is not used for motion registration to avoid errors.

Another source of blurring is jittering. A jittering pattern is a periodical change of the relative displacement between neighbored frames. A jittering pattern is detected based on decorrelation, and the results of decorrelation on motion registration are suppressed. For example, the different steering angles may offset the detected motion from actual motion, causing jittering due to the cyclical steering. When jittering is detected, the motion corrections are replaced or altered to account for the jittering. Decorrelation may also be used to determine proper registration.

A pattern of decorrelation provides a plurality of data points to detect motion, jittering, and/or proper registration. Different decorrelations throughout a sequence of frames of data indicate the decorrelation relationships throughout the sequence. Deviations from the pattern may be used to reduce jittering effects.

The examples of jittering are provided herein for steered spatial compounding. Decorrelation pattern may be used for registration in other contexts, such as different transducers being used to image a same region, extended field of view, or other situations with decorrelation of data sets due to steering changes, frequency changes, or other decorrelating variable processes.

Figure 1:
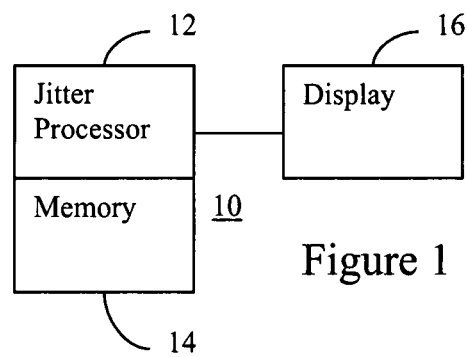
FIG. 1 is a block diagram of one embodiment of a system for reducing jittering.

FIG. 1 shows one embodiment of a system 10 for reducing jittering in medical diagnostic ultrasound imaging. The system 10 is a workstation or personal computer for operating on ultrasound data. In other embodiments, the system 10 is an ultrasound imaging system for scanning and imaging a patient.

The system 10 includes a jitter processor 12, a memory 14, and a display 16. Additional, different, or fewer components may be provided. For example, the system 10 includes a transducer and beamformer for scanning a patient with ultrasound at different angles. As another example, the system 10 includes a scan converter and/or three-dimensional image processor. In another example, a network interface is provided for retrieving frames of ultrasound data and/or for storing compounded images.

The system 10 is operable to process frames of ultrasound data. Ultrasound data includes B-mode, velocity, power, variance, Doppler flow, or other ultrasound imaging data. The ultrasound data is detected data prior to scan conversion, scan converted data prior to color look-up or gray scale conversion, or image data (e.g., RGB data). The frames correspond to a scan of a region of a patient, such as a sector, Vector®, linear, or other scan format for scanning along a plurality of scan lines spaced through a region of a patient.

The frames of data represent a two or three-dimensional region of the patent. Different frames represent the same or different regions. For example, one sequence of frames for steered spatial compounding has seven frames for seven different steering angles. The frames represent a region of about 4 cm in depth, but offset laterally due to the different steering angles.

The processor 12 is a general processor, graphics processing unit, digital signal processor, field programmable gate array, application specific integrated circuit, filter, multipliers, summer, digital circuit, analogy circuit, combinations thereof, or other now known or later developed processor. In one embodiment, the processor 12 includes an ultrasound detector, such as a B-mode or Doppler flow detector. The processor 12 receives frames of ultrasound data and processes the frames to reduce jittering, such as determining a pattern of decorrelation for detecting motion, replacing motion corrections, and/or determining alignment. The processor 12 may include a summer, filter, or other device for compounding frames of ultrasound data. While shown as one device, the processor 12 may be a plurality of devices, such as devices associated with a processing pipeline.

The processor 12 outputs a decorrelation pattern, motion corrections, and/or the frames of data as images or for conversion into images. The output for the images connects with the display 16. The display 16 is adjacent to the processor 12 or remote. The display 16 displays images associated with the component frames of data and/or a compounded image, such as a steered spatially compounded image.

The memory 14 stores ultrasound data, such as the frames of data. Processed data may be stored, such as the decorrelation pattern or motion estimates. Alternatively or additionally, the memory 14 stores instructions for operating the processor 12. For example, the memory 14 is a computer readable storage medium having stored therein data representing instructions executable by the programmed processor 12 for reducing jittering in medical diagnostic ultrasound imaging. The instructions for implementing the processes, methods and/or techniques discussed herein are provided on computer-readable storage media or memories, such as a cache, buffer, RAM, removable media, hard drive, or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 2:
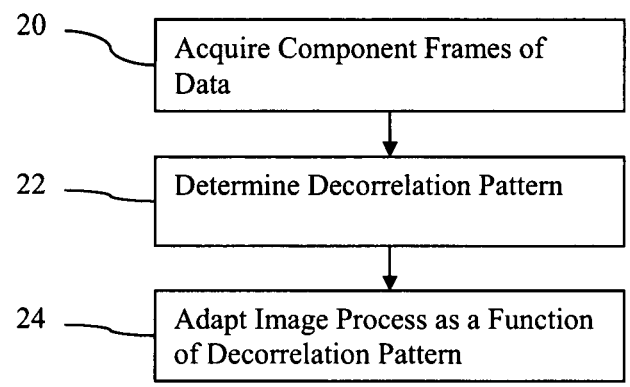
FIG. 2 is a flow chart diagram of one embodiment of a method for reducing jittering in medical diagnostic ultrasound imaging.

FIG. 2 shows one embodiment of a method for reducing jittering in medical diagnostic ultrasound imaging. Jittering is reduced by detecting and accounting for motion, by replacing jitter altered motion corrections, and/or registering frames of data to minimize jitter artifacts. The method is implemented with the system 10 of FIG. 1 or a different system. The acts are performed in the order shown or a different order. Additional, different, or fewer acts may be performed. For example, the methods of FIGS. 5 and 6 include additional acts in different embodiments of the method of FIG. 2.

In act 20, a plurality of frames of data is acquired. The frames are acquired in real-time with scanning. Alternatively, the frames are acquired from a memory. The frames represent a sequence, such as a series of frames aligned temporally in order. Alternatively, the frames may be aligned without regard to temporal relationship. The frames of data represent the same or overlapping regions of a patient. For example, the frames of data correspond to a moving aperture. As another example, the frames of data correspond to different steering angles for steered spatial compounding. Other approaches for acquiring frames of data with spatial diversity (angle, position, origin direction, or transducer position), frequency diversity, or other diversity causing periodic decorrelation may be used.

The frames of data are periodic. For example, the sequence is a repeating pattern of scanning at different steering angles (e.g., +20°, 0°, −20°, +20°, 0°, −20°, . . . ). Alternatively, the sequence does not include repetition, such as being three frames of data each with a different steering angle.

In act 22, a decorrelation pattern is detected. The decorrelation through the sequence of frames of ultrasound data is determined. Any decorrelation or lack of similarity function may be used, such as sum of absolute differences or cross-correlation. Alternatively, the decorrelation pattern is indicated by position offsets determined by a similarity function.

To form the pattern, decorrelation values between different pairs of frames of ultrasound data in the sequence are calculated. The pairs may be temporally adjacent pairs or other pairs without regard to temporal consideration. The decorrelation value is calculated between entire frames of data or between one or more regions in each frame. The frames of data are not offset or motion corrected to determine the decorrelation. Alternatively, an offset or search is provided to find a minimum decorrelation.

By determining more than one decorrelation value, a pattern of decorrelation values is provided. The pattern includes decorrelations between different pairs or other groupings of frames. In one embodiment, a frame is used for calculating two or more decorrelation values in the pattern. For example, three steered frames (+20°, 0°, −20°) are acquired. Decorrelation values are determined between +20° and 0°, −20° and 0°, and +20° and −20°. Each frame is used for two decorrelation values. Fewer decorrelation values may be determined for the three-frame example. For a repeating sequence, the decorrelation for other repetitions is based on the previous repetition (e.g., use of a reference frame or frames), is a moving window (e.g., decorrelation values for each new frame calculated relative to 2 or more (e.g., 5) previous frames), or is between all possible combinations of frames.

Figure 3:
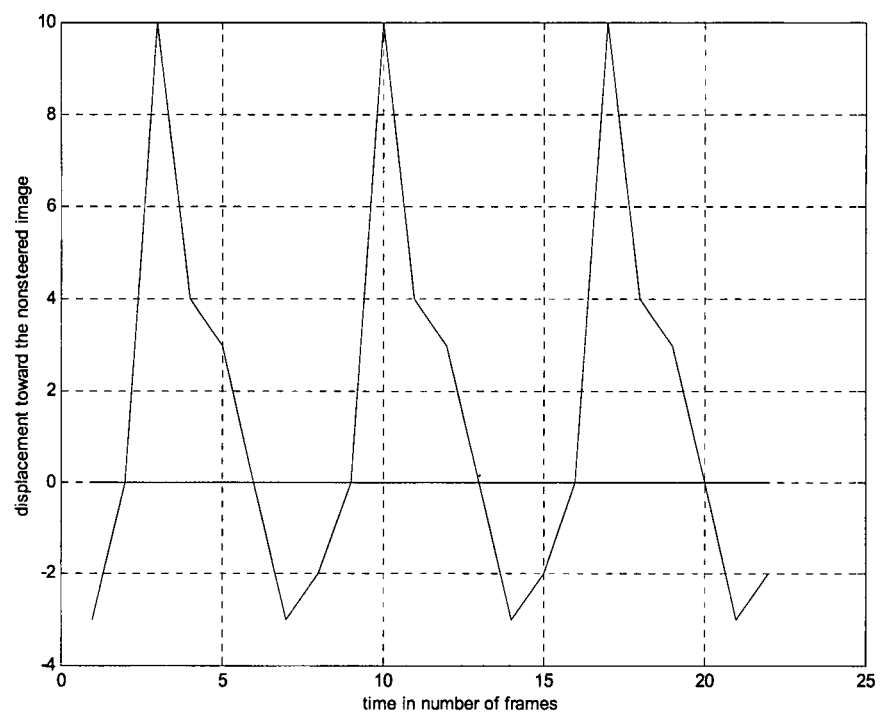
FIGS. 3 and 4 show two examples of motion jittering relative to a reference frame of data.
Figure 4:
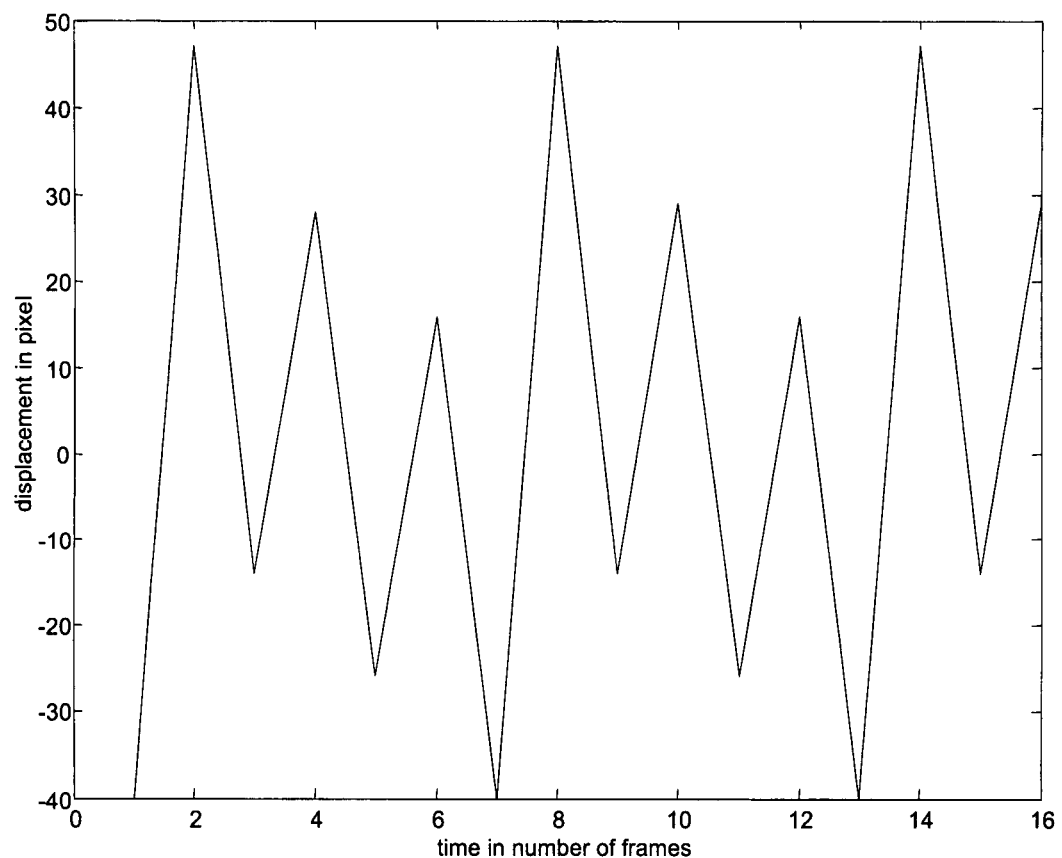

FIGS. 3 and 4 show example jittering in motion estimation, resulting from variation in decorrelation. For FIGS. 3 and 4, a repeating sequence of seven frames of data with different steering angles is used. The transducer is moved along the skin surface in an elevation direction during two-dimensional imaging, causing decorrelation in addition to the steering. Motion between frames of data is determined in the imaging plane by identifying the maximum similarity or correlation. The motion is represented along the vertical axis by number of pixels. The motion may be in one dimension (e.g., axial or lateral) or a two-dimensional motion vector. FIG. 3 shows an example of the displacement relative to a 0° or non-steered reference frame. FIG. 4 shows another example of the displacement in an ongoing manner between the two most recent frames. The motion estimation jitters or varies. The decorrelation pattern provides a similar variation. The decorrelation pattern may be the motion estimation pattern since motion estimation is based on correlation and the jittering may be the result of varied decorrelation.

Figure 5:
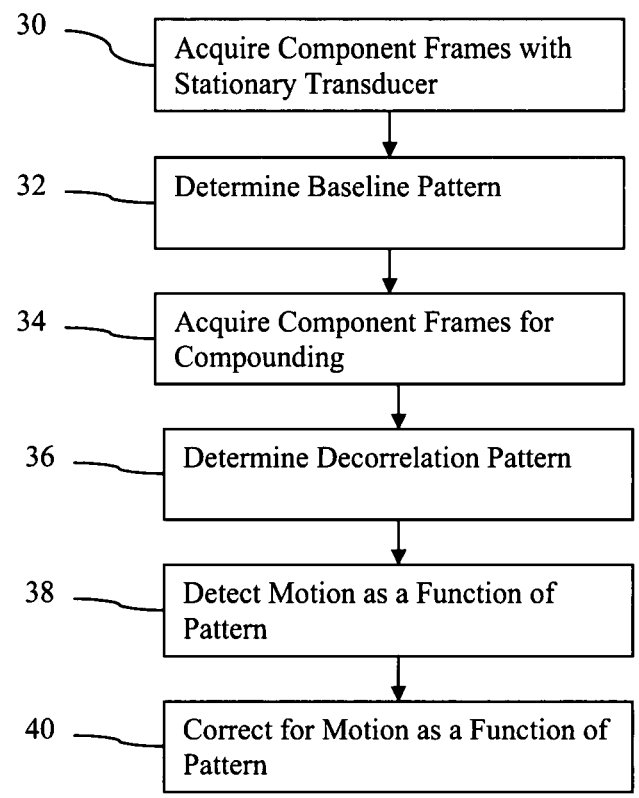
FIG. 5 shows one embodiment of adapting the imaging to the pattern in the method of FIG. 2.
Figure 6:
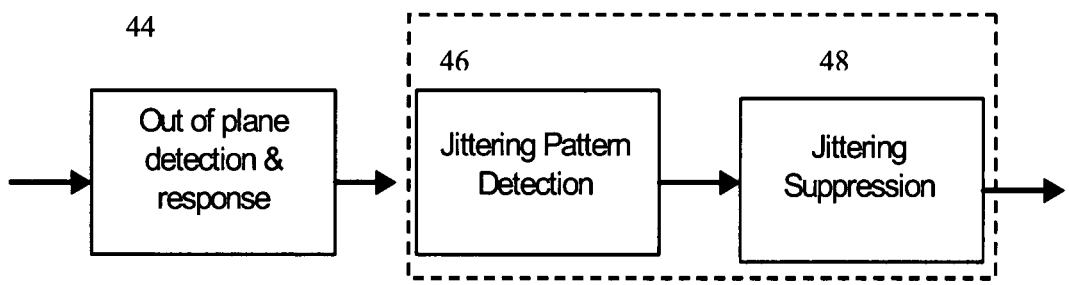
FIG. 6 shows another embodiment of adapting the imaging to the pattern the method of FIG. 2.

In act 24 of FIG. 2, ultrasound imaging adapts as a function of the pattern. Using the pattern, the adaptation reduces jittering artifacts. Any adaptation may be used. For example, the decorrelation pattern is used to detect undesired motion, such as jittering, so that the jittering may be reduced or removed. FIGS. 5 and 6 show example methods for adapting using the decorrelation pattern to detect motion. As another example, the decorrelation pattern is used to determine an optimum registration or relative motion between frames to avoid jittering artifact. FIG. 5 shows an example method for adapting to determine a more optimum registration.

The pattern of decorrelation values provides a plurality of reference points. By examining the pattern, such as the slope or other characteristic of a curve fit to the pattern or a change in sign of the decorrelation, jittering may be detected. By comparing one pattern to another pattern, jittering may be detected or used for motion estimation. The comparison is of a plurality of values or information derived from the values from one pattern to corresponding values or derived information in another pattern. If one or more values varies by a sufficient (e.g., threshold) amount, undesired or avoidable jittering may be detected or avoided. For example, multiple decorrelation values for a given frame or steering angle are calculated. If a later pattern for that frame or steering angle indicates different decorrelation for both values, jittering may be occurring. As another example, a multiple vote scheme is used. If the average or sufficient number of values is different between patterns, then jittering is detected or different alignment is desired.

FIG. 5 shows one embodiment of a method for reducing jittering in medical diagnostic ultrasound imaging. The jittering is reduced by adapting the imaging as a function of a decorrelation pattern, such as provided in act 24 of FIG. 2. Motion is detected as a function of the pattern of decorrelation through a sequence of frames. A shift in the decorrelation from a pattern acquired while the transducer is in a steady state position indicates transducer motion. The different correlation values in the steady state pattern are compared to the correlation pattern for later acquired frames. Multiple votes or values, such as two or more values of decorrelation of a frame relative to other frames or a statistic derived from multiple values, are used to detect jittering motion and/or to determine a registration or alignment minimizing jittering.

In act 30, a plurality of frames of data is acquired with a transducer in a substantially stationary position. "Substantially" accounts for breathing or other patient motion, sonographer motion, or other motion despite an attempt by at least the sonographer to maintain the transducer in one location. The frames of data establish a baseline. In one embodiment, the acquired frames of data are for steered spatial compounding, and so are associated with at least one set of component frames (e.g., +20°, 0°, −20° for a three-angle scan). Multiple repetitions of the steered scanning may be acquired for averaging of the decorrelations or multiple baseline patterns for the same combination of steering angles, but at different times. The frames of data are collected under a steady situation.

In act 32, a baseline decorrelation pattern is determined. The decorrelation across the steady state frames of data is calculated. The decorrelation pattern among the different combinations of steering angles is established. The decorrelation pattern, dp, is represented by: $dp(i,j)=f(I_i,I_j)$ where i and j are angle indexes, I is a frame of data, and f is a decorrelation function. The pattern is a set of data associated with frames of data for different combinations of steering angles. The steady state pattern is a reference pattern.

The reference pattern is the first, second, or higher order statistic of the decorrelation values. For example, the decorrelation values are used. As another example, the values are combined to provide a mean and/or variance.

The reference pattern is used throughout an image study or is updated. The updates may be for all or part of the pattern, such as updating decorrelations for steering angle combinations associated with more frequency of deviation from the reference pattern during imaging. The updates occur in response to a user trigger or to a detected event, or periodically.

In act 34, further component frames of data are acquired. The component frames of data are acquired for imaging. The further frames correspond to the different steering angles or other spatially distinct characteristic for imaging. The further component frames of data are acquired with the same settings as the reference frames, such as the same steering angles. In other embodiments, one or more parameters for acquisition are different for the reference and further frames.

The further component frames may be acquired in real time as an ongoing sequence of frames repeating the same steered scans. Alternatively, the further component frames represent a single set or partial set of frames used for compounding together.

In act 36, a second decorrelation pattern is determined across the further component frames. The pattern is aligned to start at a same steering angle as the reference pattern. The further pattern is for a single set, partial set, or more than one set of frames of data. For example, a moving window of three frames or more for a three-frame set of angles is used. The pattern for each window position is shifted to align the angles with the reference pattern for comparison.

The decorrelation function is the same or different than used for act 32. The frame combinations for the different decorrelation values are the same or different than used for act 32.

In act 38, motion of the transducer or other motion associated with jittering is detected. The motion associated with the further component frames is detected using the reference and further decorrelation patterns. To detect motion between individual component images, the decorrelation values associated with the frame of data is compared to the reference decorrelation patterns in the steady situation. If the decorrelation value or values exceed the decorrelation value or values of the reference pattern, motion is detected. If the values are sufficiently close or the patterns sufficiently similar, no motion is detected.

Any matching technique may be used to determine deviation of the further pattern from the reference pattern. For example, a curve is fit to the patterns of decorrelation values. The characteristics of the curves are compared to detect motion. In another example, a numerical comparison based on decorrelation values specific to different steering combinations is performed. If two or more, or other threshold number, of values are sufficiently different, then motion is indicated. The comparison may be of statistics of the pattern, such as comparing the mean or variance.

In act 40, motion between component frames for compounding is corrected. A translation, rotation, or translation and rotation between the component frames are determined to correct for the motion. The relative position associated with the minimum difference in the decorrelation patterns is determined. The reference pattern incorporates the substantial lack of jitter due to no transducer motion and any reference jitter due to scan process. By determining a further pattern for each possible position and comparing the patterns with the reference pattern, a motion correction accounting for the removeable jitter is determined.

To correct the motion, the minimal decorrelation (i.e., the maximum correlation) is searched in the individual component images. Using the pattern accounts for the position relative to more than one component frame. The decorrelation across multiple frames most closely matching the reference pattern indicates the desired positions. The search results of the translation, rotation, or both are applied to correct the motion.

FIG. 6 shows another embodiment of a method for reducing jittering in medical diagnostic ultrasound imaging. The jittering is reduced by adapting the imaging as a function of a decorrelation pattern, such as provided in act 24 of FIG. 2. Motion is detected as a function of the pattern of decorrelation through a sequence of frames. Variation in the decorrelation indicates jitter. To avoid incorporating the jitter into the motion corrections, a substitute or low pass filtered motion is used. The motion is corrected using the pattern of decorrelation. If the pattern shows the motion jittering, the contribution of the motion jittering is reduced, such as by replacing the motion.

Figure 7:
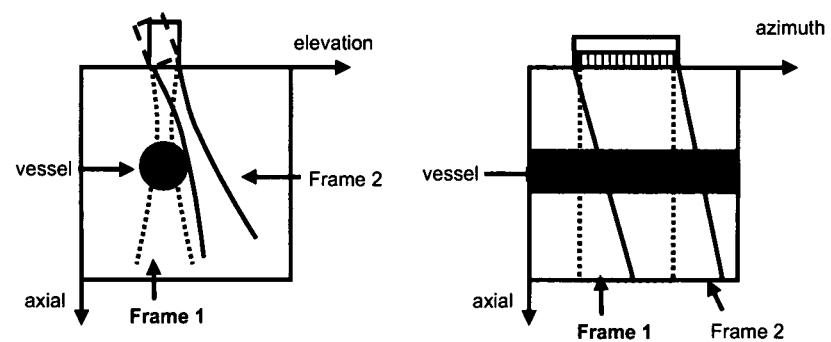
FIG. 7 is an example illustration of out-of plane and in-plane motion.

In act 44, substantial out-of-plane motion is detected. When clinicians move a one-dimensional transducer array in the elevation direction or the array is tilted in a certain angle with azimuth as the rotating axis during compounding image acquisition, the frames may have no or little speckle correlation and similarity. FIG. 7 shows elevation-axial and azimuth-axial positions of two frames of data. By tilting the transducer, Frame 2 has little overlap with Frame 1. While intended to image a vessel, Frame 2 does not intersect the vessel due to elevation movement. Frames 1 and 2 are shown with different (e.g., 0 and 20 degree) steering. Frame 2 is very decorrelated with Frame 1, so alignment is unlikely. In this case, the correlation for motion tracking may result in a false alarm motion that can cause severe jittering artifacts. Motion correction may not be capable of correcting blur. Instead, the frame is discarded or compounded with the resulting blur without further attempts at motion correction.

A threshold amount of decorrelation is detected between frames prior to identifying any motion. For the threshold or higher amount in act 44, compounding is avoided since the decorrelation may indicate large out-of-plane motion. The similarity of the two frames with different steering angles is calculated. If sufficiently decorrelated, then detected motion will be ignored.

In one embodiment, the out-of-plane situation is detected and the estimated motion is ignored. Define s1 as the ROI in frame 1 and s2 as the ROI in frame 2. Given a tracking step size a in both azimuth and axial direction, the sum of absolute differences (SAD) or other method is applied for calculating 2D correlation between s1 and s2. The position where SAD takes the minimum value gives the relative motion between frame 1 and frame 2 in both azimuth and axial direction. Define the minimum value of SAD as min_SAD, then out-of-plane can be detected if the maximum(min_SAD/$\Sigma$|s1|, min_SAD/$\Sigma$|s2|)>threshold, where $\Sigma$|s1| and $\Sigma$|s2| are the sum of absolute values for pixels in s1 and s2. The threshold is an empirical parameter, generally, in a range of 0.2~0.6. Frame 1 and frame 2 are out-of-plane relatively if the maximum of the two minimum SAD calculations is above the threshold. The detected motion is ignored.

Figure 8:
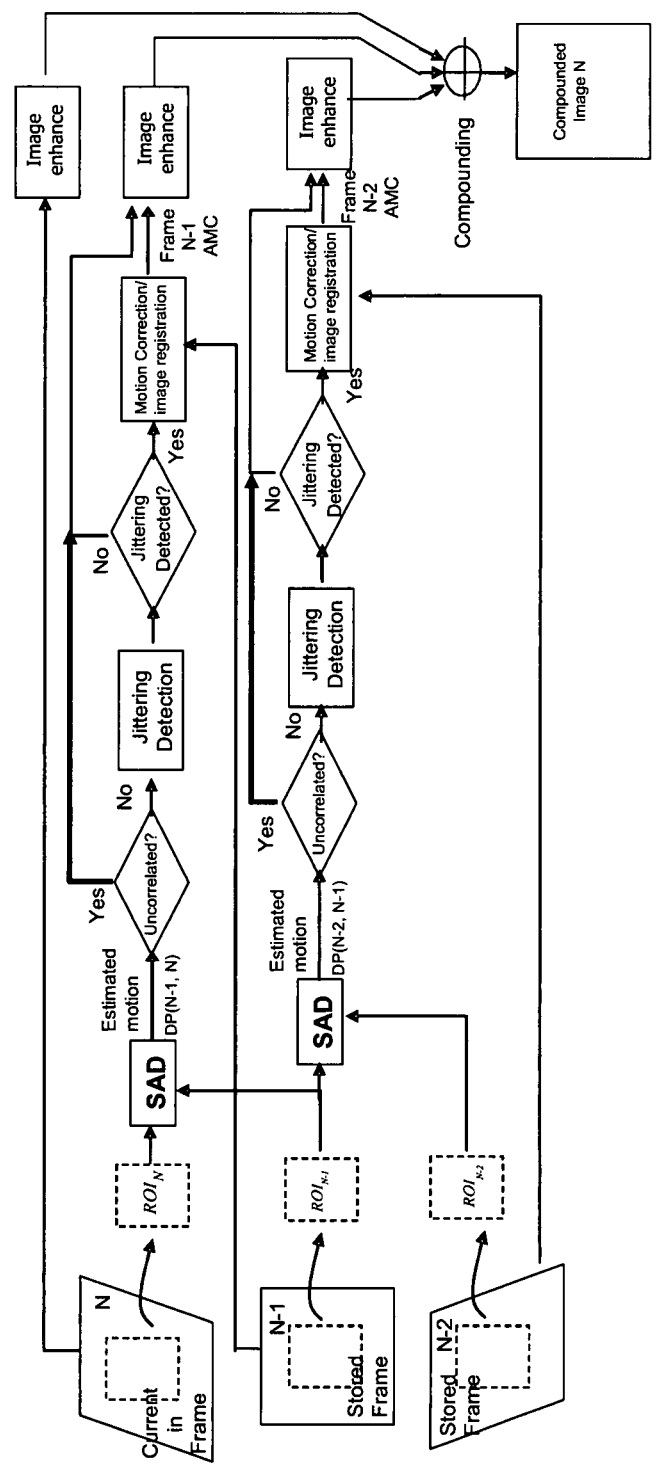
FIG. 8 is a flow chart diagram of one example embodiment of the method of FIG. 6.

FIG. 8 shows one example. Three frames of data are acquired. Using a region of interest, the sum of absolute differences is used to determine a level of similarity between Frame N and N−1 and between Frame N−1 and N−2. If the level of similarity shows the frames to be sufficiently decorrelated, then motion correction between the two pairs of frames is skipped rather than discarding the frames.

Jittering detection of act 46 (FIG. 6), such as detection of undesired but correctable motion, may be implemented after discarding frames of data associated with no or very little correlation. The jittering detection process occurs after the motion estimation or decorrelation act 44 and before the motion compensation act 48.

In act 46, a jitter in motion estimation is identified for a sequence of frames. For example, frames of data associated with different steering angles are correlated. The amount of decorrelation may indicate jitter. For example, the decorrelation has a change of slope corresponding to a change in sign of the motion estimation through the sequence. The jittering pattern is detected after motion estimation based on the saw tooth like periodical displacement or varying change characteristic.

The jittering pattern is identified by looking for a saw tooth like periodical varying displacement or any other specific characteristics observed empirically. The change in decorrelation across the sequence of frames shows the presence of jitter. By examining the decorrelation pattern formed from the out-of-plane or other similarity measure, undesired motion is detected.

The detection is performed in real time or as frames are acquired. The amount of decorrelation between any two frames may or may not indicate jitter, so the pattern of decorrelation across multiple frames of the sequence is used. Non-real time detection may be used.

Jittering artifacts have some special characteristics that can be identified and used for detection and suppression. For example, the non-steered (center) frame is used as a reference frame, and $TM_0(k)$ as the estimated motion in azimuth and/or axial direction between current frame k and the nearest non-steered frame o in time. The estimated motion includes searching for a highest similarity relative position. In alternative embodiments, the decorrelation without identifying a best displacement is used. $TM_0(k)$ is measured with displacement pixels, but other measures of displacement (e.g., distance) may be used. The jittering artifacts create periodical displacement change for $TM_0(k)$, such as shown in FIGS. 3 and 4.

Pattern recognition methods, a change in sign (e.g., decorrelation slope), or other detection may be used. For example, if the saw tooth is as shown in FIG. 4, the detection scheme may be performed in two steps. For a current frame k, the tracked motion derivation with 3 previous frames is calculated:

$$diff_1 = TM_0(k) - TM_0(k-1);$$

$$diff_2 = TM_0(k-1) - TM_0(k-2);$$

$$diff_3 = TM_0(k-2) - TM_0(k-3);$$

The differences $diff_1$, $diff_2$, $diff_3$ indicate the decorrelation. The sign of the differences is examined. If the sign changes, jittering is present in these 4 frames:

If $sign(diff_1) = sign(diff_3)$ and $sign(diff_2) \ne sign(diff_1)$ then the saw tooth pattern detected.

For the saw tooth pattern shown in FIG. 3, more sophisticated pattern recognition methods may be used, such as correlating with possible patterns, a trained neural network, or other pattern recognition. Data from multiple cycles or repetitions of the scan sequence may be used, such as processing frames for at least two cycles. Separate detections of motion are performed to confirm motion or the patterns are combined prior to detection.

Further, the jittering artifacts may create other types of characteristics that are different than the periodically varied saw tooth shape. However, patterns may be developed to recognize such artifacts.

In the example of FIG. 8, jittering is detected or not. If jittering is detected, then the motion is corrected. If jittering is not detected, then the determined motion or displacement is used without further correction for jittering.

In act 48 of FIG. 6, the detected jitter in the motion estimation is reduced or removed. For example, the motion estimation associated with jitter is replaced with an average or a low-pass filtered value. The motion estimates associated with the same steering but other cycles or across the sequence regardless of steering are averaged or low-pass filtered. In one embodiment, the average is the average of motion between frames of one cycle of a steered compound scan (i.e., across the component frames of all the steering angles used for compounding).

The amount of averaging and/or filtering may vary as a function of the amount of jitter detected. The type of detected jittering may indicate different reductions or actions to reduce jittering. In an alternative embodiment, the displacement associated with jitter is ignored so that no motion is assumed to have occurred. In other embodiments, the motion estimate is updated, such as by weighting the motion estimate by a weight that is a function of the decorrelation level. A predetermined or set motion estimate may be used in other embodiments. An extrapolated or interpolated motion estimate from other cycles or a reference cycle may be used. The replacement motion may suppress or eliminate jittering artifacts.

In the example of FIG. 8, the frames of data are registered based on the corrected motion estimates. The frames of data are translated and/or rotated relative to each other based on the corrected motion. Any image enhancement is provided, such as filtering or weighting to account for different locations being associated with different number of component frames. The aligned or registered frames of data are then compounded. The resulting compounded image may have less blurring due to reduction of jitter.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed:

1. A method for reducing jittering in medical diagnostic ultrasound imaging, the method comprising:
    determining decorrelation values through a sequence of frames of ultrasound data, a collection of the decorrelation values being a pattern comprising a plurality of data points representing different decorrelation values between different groupings of the frames of the sequence;
    distinguishing a periodical variation characteristic represented in the pattern of the decorrelation values through the sequence from random jitter variation represented in the pattern of the decorrelation values due to external motion or noise; and
    adapting ultrasound imaging as a function of the jitter as distinguished from the periodical characteristic of the different decorrelation values of the pattern.

2. The method of claim 1 wherein determining the pattern comprises determining decorrelation values between different pairs of frames of ultrasound data in the sequence, the pattern comprising the decorrelation values between at least two different pairs of frames of ultrasound data.

3. The method of claim 2 wherein determining the decorrelation values comprises determining between the different pairs, each pair having one frame of ultrasound data in common with another pair.

4. The method of claim 1 wherein the sequence of frames of ultrasound data comprises a sequence of frames for steered spatial compounding, and wherein adapting comprises reducing jittering artifacts as a function of the pattern.

5. The method of claim 1 wherein adapting comprises:
detecting motion as a function of the pattern; and
correcting for the motion between at least two of the frames of ultrasound data.

6. The method of claim 5 wherein determining comprises determining the pattern with a transducer being held in a steady state position, and wherein detecting motion comprises detecting transducer motion by a shift in decorrelation from the pattern in the steady state position.

7. The method of claim 5 wherein determining comprises determining the pattern with a transducer being held in a steady state position, and wherein correcting for motion comprises identifying a translation, rotation, or translation and rotation providing a minimum difference in decorrelation from the pattern.

8. The method of claim 5 wherein detecting comprises detecting as a function of at least two decorrelation values associated with different sets of frames of ultrasound data, the different sets having at least one frame of ultrasound data in common.

9. The method of claim 1 wherein adapting comprises:
determining a motion between the frames of ultrasound data within the sequence; and
correcting the motion as a function of the pattern.

10. The method of claim 9 wherein correcting comprises reducing a contribution of motion jittering through the sequence if the pattern shows the motion jittering.

11. The method of claim 10 wherein reducing comprises replacing the motion.

12. The method of claim 1 wherein adapting comprises changing where a subsequent pattern of a plurality of additional data points of decorrelation values deviates from the pattern of the plurality of data points representing the decorrelation values.

13. In a non-transitory computer readable storage medium having stored therein data representing instructions executable by a programmed processor for reducing jittering in medical diagnostic ultrasound imaging, the storage medium comprising instructions for:
estimating relative motion between frames of ultrasound data through a sequence of the frames;
identifying a jitter in the estimated motion for the sequence of frames of ultrasound data where different ones of the frames in the sequence are associated with different steering angles than other ones of the frames in the sequence for steered spatial compounding, the different ones of the frames with the different steering angles each having a different one of the steering angles than the other ones of the frames;
reducing the jitter in values of the estimated motion; then
spatially aligning the frames based on the values of the estimated motion after reducing the jitter; and
steered spatially compounding the frames of the sequence as spatially aligned based on the values of the estimated motion with reduced jitter, the compounding comprising combining data from a plurality of the frames of the sequence into a compounded frame of data that is a function of the plurality of the frames of the sequence.

14. The non-transitory computer readable storage medium of claim 13 wherein identifying the jitter comprises explicitly identifying that a sign change of the motion estimation through the sequence has occurred.

15. The non-transitory computer readable storage medium of claim 13 wherein reducing comprises replacing a motion estimation value associated with jitter with an average or low-pass filtered value.

16. The non-transitory computer readable storage medium of claim 13 further comprising:
detecting motion as a function of a pattern of decorrelation through the sequence of frames.

17. The non-transitory computer readable storage medium of claim 13 further comprising:
detecting a threshold amount of decorrelation between frames prior to identifying; and
avoiding the compounding in response to the detecting and providing the compounding in response to a failure to detect the threshold amount of decorrelation.

18. In a non-transitory computer readable storage medium having stored therein data representing instructions executable by a programmed processor for reducing jittering in medical diagnostic ultrasound imaging, the storage medium comprising instructions for:
acquiring, with a substantially stationary transducer, first component frames of data for steered spatial compounding, the component frames of data corresponding to different steering angles, the first component frames with the different steering angles each having a different one of the steering angles than the other ones of the first component frames;
determining a first decorrelation pattern across the first component frames, the first decorrelation pattern comprising a plurality of data points representing different decorrelation values between different groupings of the frames of the sequence;
acquiring second component frames of data corresponding to the different steering angles, the second component frames with the different steering angles each having a different one of the steering angles than the other ones of the second component frames;
determining a second decorrelation pattern across the second component frames, the second decorrelation pattern comprising a plurality of data points representing different decorrelation values between different groupings of the frames of the sequence;
comparing the first decorrelation pattern with the second decorrelation pattern, the comparing distinguishing a periodical variation characteristic represented in the first decorrelation pattern from motion variation represented in the second decorrelation pattern; and
detecting motion of the transducer for the second component frames as the motion variation with the periodical characteristic of the first decorrelation pattern removed from the second decorrelation pattern.

19. The non-transitory computer readable storage medium of claim 18 further comprising:
correcting for the motion as a function of the first decorrelation pattern.

20. The non-transitory computer readable storage medium of claim 18 further comprising:
identifying a jittering in the motion; and
correcting for the motion with a replacement motion value.

21. The non-transitory computer readable storage medium of claim 18 further comprising:
compounding the second component frames as a function of the motion.

* * * * *